United States Patent
Chung et al.

(10) Patent No.: US 7,279,492 B2
(45) Date of Patent: Oct. 9, 2007

(54) S-(−)-AMLODIPINE NICOTINATE AND PROCESS FOR THE PREPARATION THEREOF

(75) Inventors: You Sup Chung, Suwon (KR); Mun Choun Ha, Yongin (KR)

(73) Assignee: Hanlim Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 10/527,093

(22) PCT Filed: Sep. 8, 2003

(86) PCT No.: PCT/KR03/01850

§ 371 (c)(1),
(2), (4) Date: Mar. 9, 2005

(87) PCT Pub. No.: WO2004/024690

PCT Pub. Date: Mar. 25, 2004

(65) Prior Publication Data

US 2006/0014795 A1    Jan. 19, 2006

(30) Foreign Application Priority Data

Sep. 11, 2002  (KR) .................. 10-2002-0054809
Jan. 9, 2003   (KR) .................. 10-2003-0001260

(51) Int. Cl.
*A61K 31/44*     (2006.01)
*C07D 213/803*   (2006.01)

(52) U.S. Cl. ........................ 514/356; 546/321

(58) Field of Classification Search ............... 546/321; 514/356
See application file for complete search history.

(56) References Cited

U.S. PATENT DOCUMENTS

| 4,285,955 A | 8/1981 | Wehinger et al. |
|---|---|---|
| 4,572,909 A | 2/1986 | Campbell et al. |
| 4,879,303 A | 11/1989 | Davison et al. |
| 6,291,490 B1 | 9/2001 | Young |
| 6,333,342 B1 * | 12/2001 | Foster ............... 514/356 |
| 6,699,892 B2 * | 3/2004 | Lee et al. ............ 514/356 |
| 6,828,339 B2 * | 12/2004 | Ettema et al. ........ 514/356 |
| 2003/0225143 A1 | 12/2003 | Lee et al. |

FOREIGN PATENT DOCUMENTS

| CN | 1343663 | 4/2002 |
|---|---|---|
| EP | 0089167 A2 | 9/1983 |
| EP | 0 244 944 A2 | 11/1987 |
| WO | WO 93/10779 A | 6/1993 |
| WO | 03043989 A1 | 5/2003 |

OTHER PUBLICATIONS

Database Caplus, Chemical Abstracts Service; retrieved from STN, Database accession No. 2003:431739, * abstract *, & CN 1 343 663 A (J. FU), Apr. 10, 2002, XP002397381.
Budavari, et al. (eds.) The Merck Index, 11th Edition, 1989, p. 81.

* cited by examiner

*Primary Examiner*—Patricia L. Morris
(74) *Attorney, Agent, or Firm*—Rothwell, Figg, Ernst & Manbeck

(57) ABSTRACT

The present invention provides a novel salt of S-(−)-amlodipine, i.e., a nicotinic acid salt of S-(−)-amlodipine, a process for preparing the same, and a pharmaceutical composition comprising the same as an active ingredient.

2 Claims, 10 Drawing Sheets

FIG. 2

| CAPTION %n | LEGEND k1 2-THETA | ANGLE D VALUE ANGSTROM | INTENSITY | INTENSITY COUNT % |
|---|---|---|---|---|
| 8.87024 | 8.87024 | 9.96118 | 17.4 | 49.5 |
| 12.40769 | 12.40769 | 7.12805 | 17.8 | 50.5 |
| 13.25102 | 13.25102 | 6.67623 | 35.2 | 100.0 |
| 14.65376 | 14.65376 | 6.04015 | 9.04 | 25.7 |
| 17.44421 | 17.44421 | 5.07972 | 9.18 | 26.1 |
| 19.73034 | 19.73034 | 4.49600 | 9.89 | 28.1 |
| 20.34481 | 20.34481 | 4.36157 | 9.58 | 27.2 |
| 21.99343 | 21.99343 | 4.03821 | 16.4 | 46.5 |
| 22.48365 | 22.48365 | 3.95126 | 18.2 | 51.7 |
| 24.65381 | 24.65381 | 3.60814 | 12.0 | 34.1 |
| 26.70359 | 26.70359 | 3.33565 | 13.4 | 38.0 |
| 28.63978 | 28.63978 | 3.11439 | 6.91 | 19.6 |
| 39.56902 | 39.56902 | 2.27574 | 5.16 | 14.6 |
| 61.45071 | 61.45071 | 1.50766 | 2.90 | 8.2 |

S-(−)-AMLODIPINE NICOTINATE AND PROCESS FOR THE PREPARATION THEREOF

CROSS REFERENCE TO RELATED APPLICATION

This application is a 35 U.S.C. § 371 National Phase Entry Application from PCT/KR03/001850, filed Sep. 8, 2003, and designating the U.S.

BACKGROUND OF THE INVENTION

1. Field of the Invention

The present invention relates to a novel salt of S-(−)-amlodipine, more specifically, to a nicotinic acid salt of S-(−)-amlodipine, a process for preparing the same, and a pharmaceutical composition comprising the same as an active ingredient.

2. Description of the Related Art

Amlodipine, with a chemical name of 3-ethyl 5-methyl 2-[(2-aminoethoxy)methyl]-4-(2-chlorophenyl)-1,4-dihydro-6-methylpyridine-3,5-dicar boxylate, is a potent and long-acting calcium channel blocker useful as an anti-ischaemic and anti-hypertensive agent. It is known that the two enantiomers of amlodipine have different pharmacological profiles. The S-(−)-isomer is the more potent calcium channel blocker, while the R-(+)-isomer also exhibits activity in the treatment or prevention of atherosclerosis.

Although amlodipine is effective as a free base form, in practice, it is administered in a form of a pharmaceutically acceptable acid addition salt. Such a pharmaceutically acceptable salt of amlodipine must satisfy pharmaceutical characteristics, such as solubility, stability, non-hygroscopicity, processability for tablet formulation.

EP 89,167 and U.S. Pat. No. 4,572,909 disclose various pharmaceutically acceptable salt forms of amlodipine. For example, pharmaceutically acceptable acid addition salts are disclosed, formed from acids which form non-toxic acid addition salts containing pharmaceutically acceptable anions, such as the hydrochloride, hydrobromide, sulfate, phosphate or acid phosphate, acetate, maleate, fumarate, lactate, tartrate, citrate and gluconate salts. Further, among them, maleate salt is disclosed as a preferable salt.

EP 244,944 and U.S. Pat. No. 4,879,303 disclose that benzene sulphonate salt of amlodipine (amlodipine besylate) has a number of advantageous physicochemical properties over the maleate salt thereof, such as good solubility, good stability, non-hygroscopicity, and processability for tablet formulation.

U.S. Pat. No. 6,291,490 discloses a method of treating a condition by excessive calcium influx in cells in a human, which comprises administering to said human in need of such therapy a therapeutically effective amount of (−) amlodipine, i.e., S-(−)-amlodipine or a pharmaceutically acceptable salt thereof. Further, U.S. Pat. No. 6,291,490 also discloses that such acid salt include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, and p-toluenesulfonic. And also, it discloses that particularly preferred are besylate, hydrobromic, hydrochloric, phosphoric and sulfuric acids.

However, according to the present inventors' experiments, the salts of S-(−)-amlodipine disclosed in the above, e.g., S-(−)-amlodipine besylate, do not have sufficient photostability.

SUMMARY OF THE INVENTION

The present invention provides a novel S-(−)-amlodipine salt, i.e., S-(−)-amlodipine nicotinate, which has an improved photostability; and an enhanced pharmacological activity.

Further, the present invention provides a process for preparing the nicotinic acid salt of S-(−)-amlodipine and a pharmaceutical composition comprising S-(−)-amlodipine nicotinate.

In one aspect of the present invention, there is provided a nicotinic acid salt of S-(−)-amlodipine (i.e., S-(−)-amlodipine nicotinate).

In another aspect of the present invention, there is provided a process for preparing S-(−)-amlodipine nicotinate, which comprises reacting S-(−)-amlodipine with nicotinic acid in an organic solvent.

In still another aspect of the present invention, there is provided a process for preparing S-(−)-amlodipine nicotinate anhydrate, which comprises drying a hydrous form of S-(−)-amlodipine nicotinate.

In still another aspect of the present invention, there is provided a pharmaceutical composition for anti-ischaemia or anti-hypertension comprising a therapeutically effective amount of S-(−)-amlodipine nicotinate and a pharmaceutically acceptable carrier.

BRIEF DESCRIPTION OF THE DRAWINGS

The above and other features and advantages of the present invention will become more apparent by describing in detail exemplary embodiments thereof with reference to the attached drawings in which:

FIG. 2 shows peak list data of the X-ray diffraction chart;

DETAILED DESCRIPTION OF THE INVENTION

Figure 1:
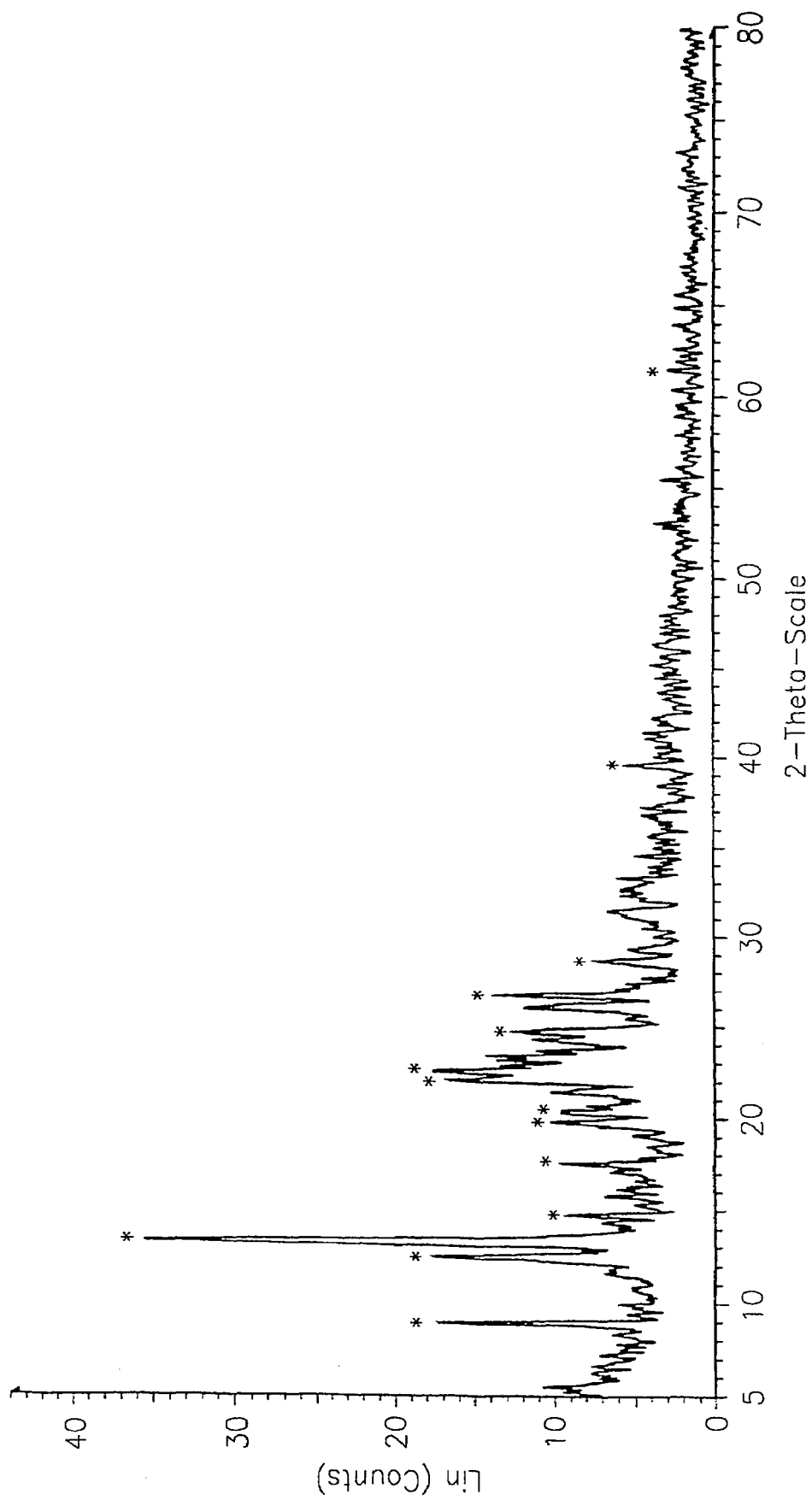
FIG. 1 shows an X-ray diffraction chart of S-(−)-amlodipine nicotinate.

The nicotinic acid salt of amlodipine according to the present invention has a following chemical structure:

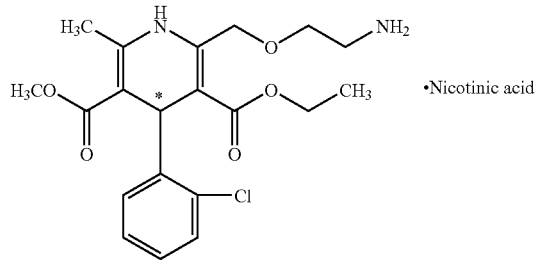

S-(−)-Amlodipine nicotinate of the present invention may be in an anhydrous form or a hydrous form. Preferably, S-(−)-amlodipine nicotinate is amlodipine nicotinate dihydrate ($2H_2O$), more preferably amlodipine nicotinate dihydrate having an X-ray diffraction pattern of FIG. 1.

S-(−)-Amlodipine nicotinate of the present invention has good physicochemical properties such as good solubility, good stability, non-hygroscopicity, and processability for tablet formulation.

Further, S-(−)-amlodipine nicotinate of the present invention has a high photostability and an enhanced pharmacological activity, which are clear from various Examples to be described afterwards.

The present invention also includes, within its scope, a process for preparing S-(−)-amlodipine nicotinate. That is, the present invention provides a process for preparing S-(−)-amlodipine nicotinate, which comprises reacting S-(−)-amlodipine with nicotinic acid in an organic solvent.

In the process of the present invention, the organic solvent used includes any conventional solvent capable of dissolving both S-(−)-amlodipine and nicotinic acid, such as $C_1$-$C_5$ alkanol including methanol, ethanol, isopropanol etc. Further, the organic solvent used includes a conventional solvent containing water, e.g., 95% industrial methylated spirit, etc.

The process of the present invention may further comprise a re-crystallization step. Preferably, a mixed solvent of methanol and isopropanol or water and isopropanol is used. When a mixed solvent of methanol and isopropanol is used, methanol and isopropanol may be mixed in a ratio of about 1:9 to 2:8 by volume. When a mixed solvent of water and isopropanol is used, water and isopropanol may be mixed in a ratio of about 3:97 to 5:95 by volume. However, the mixing ratios of the solvents may vary according to a person skilled in the art.

Further, the present invention provides a process for preparing S-(−)-amlodipine nicotinate anhydrate, which comprises drying a hydrous form of S-(−)-amlodipine nicotinate. The drying step may be performed under a reduced pressure and at 115-125° C.

The present invention includes, within its scope, a pharmaceutical composition for anti-ischaemia or anti-hypertension comprising a therapeutically effective amount of S-(−)-amlodipine nicotinate and a pharmaceutically acceptable carrier.

The pharmaceutical composition of the present invention may be administered orally or parenterally. The pharmaceutical composition for oral administration may be in various forms such as tablets, capsules, granules, and solutions, which may further contain conventional additives such as a diluent, disintegrant, lubricant and the like. The composition for parenteral administration (e.g., injection) may be an isotonic solution, and may be sterilized and/or may contain a conventional adjuvant such as a preservative, stabilizer and the like.

The pharmaceutical composition of the present invention may be administered for the treatment of ischaemia or hypertension in a dosage of about 2-50 mg/day for an average adult of about 70 kg weight, although the dosage may vary in accordance with the kind and severity of a disease to be treated. Thus, for a typical adult patient, individual tablets or capsules may contain about 1 to 10 mg of S-(−)-amlodipine nicotinate, in a suitable pharmaceutically acceptable carrier. Dosages for intravenous administration would be about 1 to 10 mg per single dose as necessary.

Although the present invention may be more detailed explained by reference to the following Examples, the following Examples are not intended to limit the scope of the present invention.

EXAMPLE 1

Preparation of S-(−)-amlodipine Nicotinate Dihydrate

The solution of S-(−)-amlodipine (2.0 g, 4.89 mmole) in 95% industrial methylated spirit (10.0 ml) was added to the slurry of nicotinic acid (602 mg, 4.89 mmole) in 95% industrial methylated spirit (2.5 ml). The solution was slowly heated and then refluxed for 5 hours. The reaction mixture was cooled to 5° C. to form S-(−)-amlodipine nicotinate hydrate, which was then filtered and washed with industrial isopropanol (5.0 ml).

The resulting salt was heated and dissolved in the mixed solvent (10 ml) of 95% methanol and isopropanol (1:9 by volume). The resulting solution was slowly stirred at a room temperature and cooled to 0° C. to produce a precipitate, which was then filtered, washed with isopropanol (5.0 ml), and dried under a reduced pressure and at 80° C. for 5 hours to give 2.2-2.26 g of S-(−)-amlodipine nicotinate.

Yield: 79.3-81.4% Melting Point: 178-180° C. $^1$H-NMR ($CDCl_3$) 9.19(s, 1H), 8.63(d, 1H), 8.24(d, 1H), 7.75(s, 1H), 6.97-7.34(m, 5H), 5.33(s, 1H), 4.74(gq, 2H), 4.01(m, 2H), 3.76(bs, 2H), 3.55(s, 3H), 3.17(bs, 2H), 2.28(s, 3H), 1.15(t, 3H) $[\alpha]_D^{25}$=−24.4 (c=1, MeOH)

200 mg of S-(−)-amlodipine nicotinate obtained in the above process was dried at 120° C. and under a reduced pressure of lower than 5 mmHg for 5 hours and afterwards, the loss on dry (LOD) thereof was measured. As a result, the obtained S-(−)-amlodipine nicotinate in Example 1 was in the form of S-(−)-amlodipine nicotinate dihydrate.

Further, the X-ray diffraction of the product obtained in the above process, which was measured with Rigaku Rotaflex 12Kw XRD-2000, is shown in FIG. 1 and the peak list data thereof are shown in FIG. 2.

EXAMPLE 2

Preparation of S-(−)-amlodipine Nicotinate dihydrate

The procedure of Example 1 was repeated, except for using the mixed solvent (10 ml) of water and isopropanol (5:95 by volume) in place of the mixed solvent (10 ml) of 95% methanol and isopropanol (1:9 by volume), to obtain 2.1 g of S-(−)-amlodipine nicotinate dihydrate.

EXAMPLE 3

Preparation of S-(−)-amlodipine Nicotinate Anhydrate

S-(−)-Amlodipine nicotinate dihydrate obtained in Example 1 was dried under a reduced pressure and at 115-125° C. for 5 hours to give S-(−)-amlodipine nicotinate anhydrate.

Melting Point: 179-181° C.

| | | | |
|---|---|---|---|
| Calc. | C; 58.70 | H; 5.68 | N; 7.90 |
| Found | C; 58.65 | H; 5.60 | N; 7.91 |

TEST EXAMPLE 1

Figure 3A:
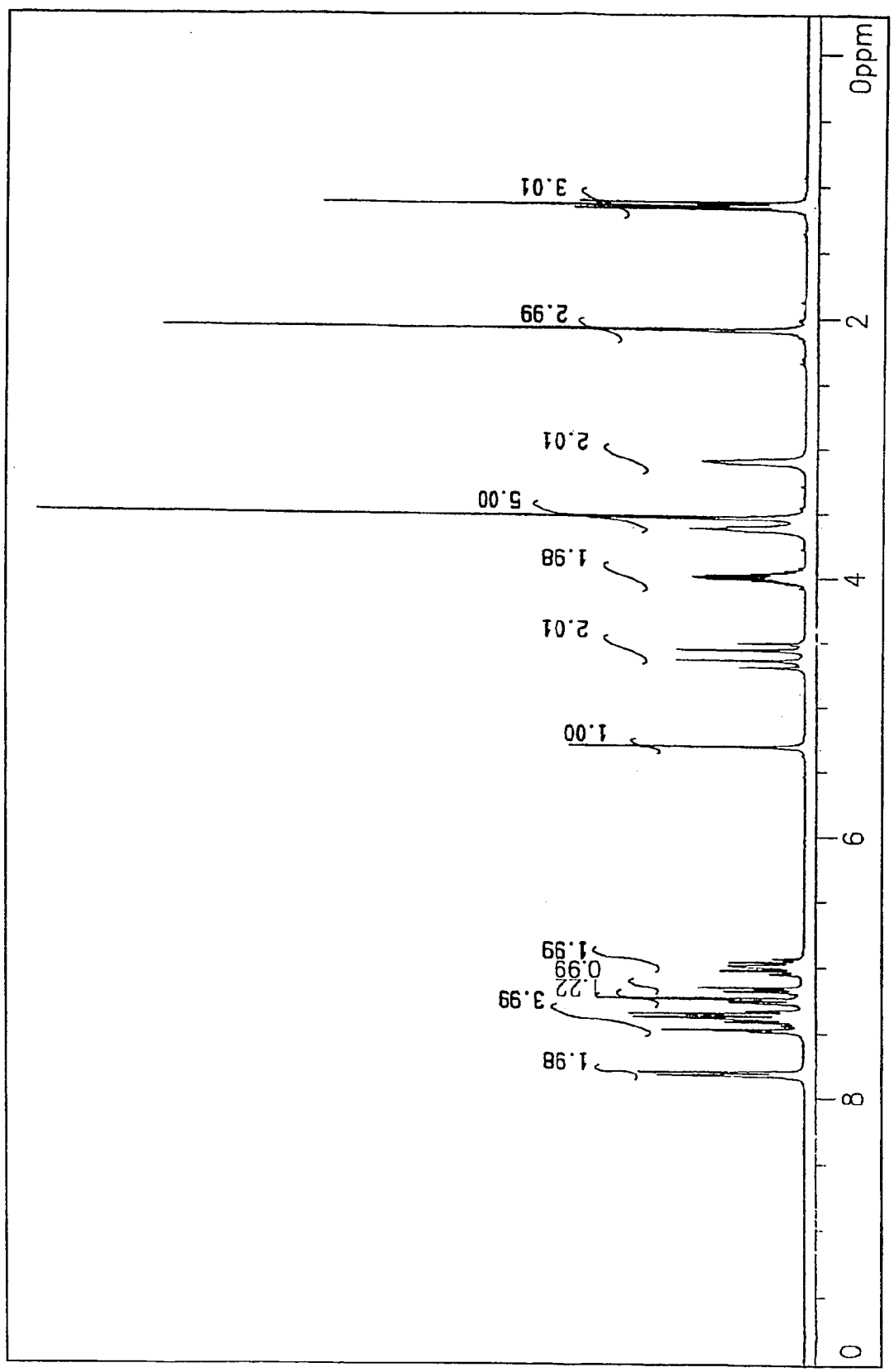
FIGS. 3A, 3B, 3C, and 3D show $^1$H-NMR charts of S-(−)-amlodipine besylate and after photostability test, respectively.
Figure 3B:
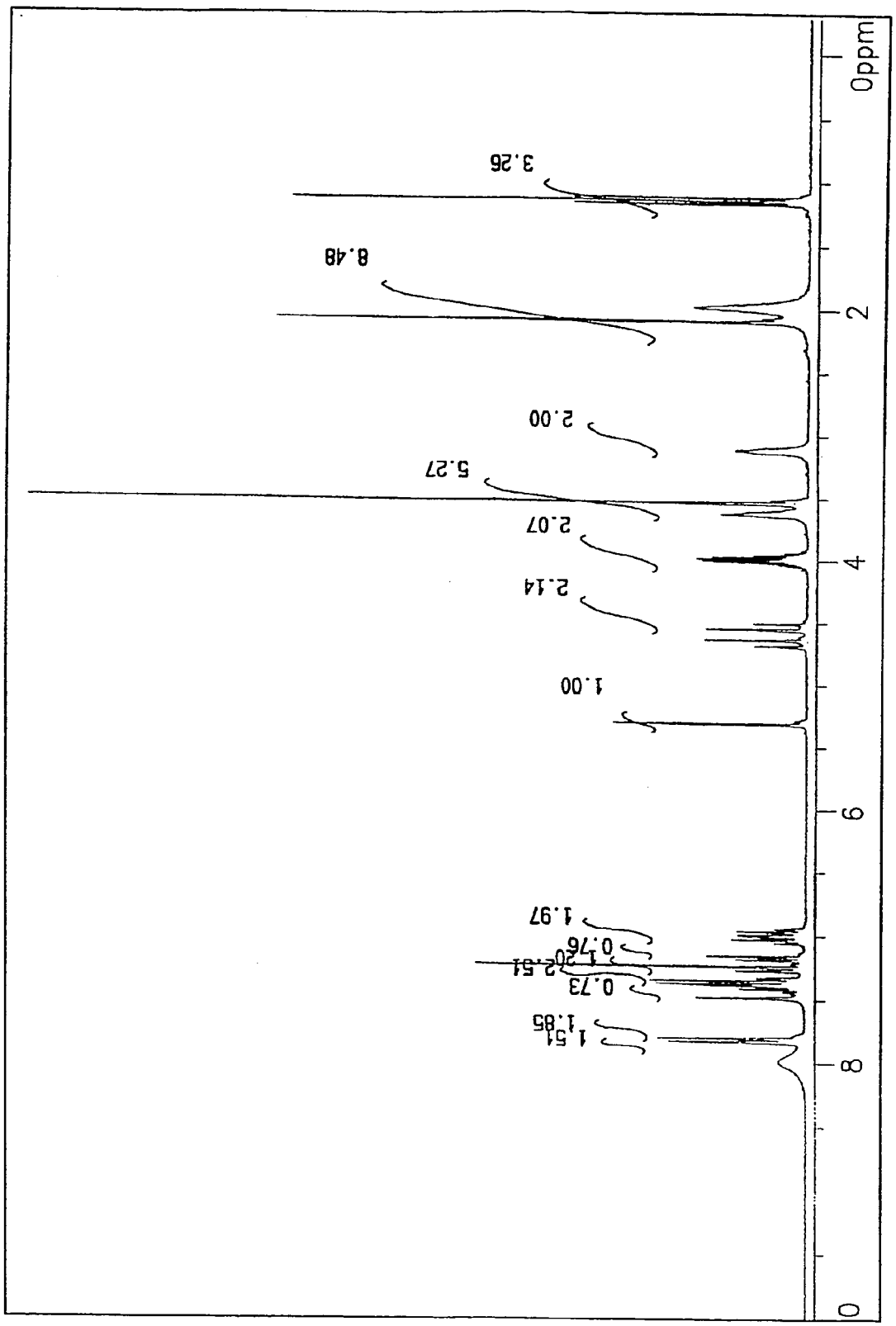
Figure 3C:
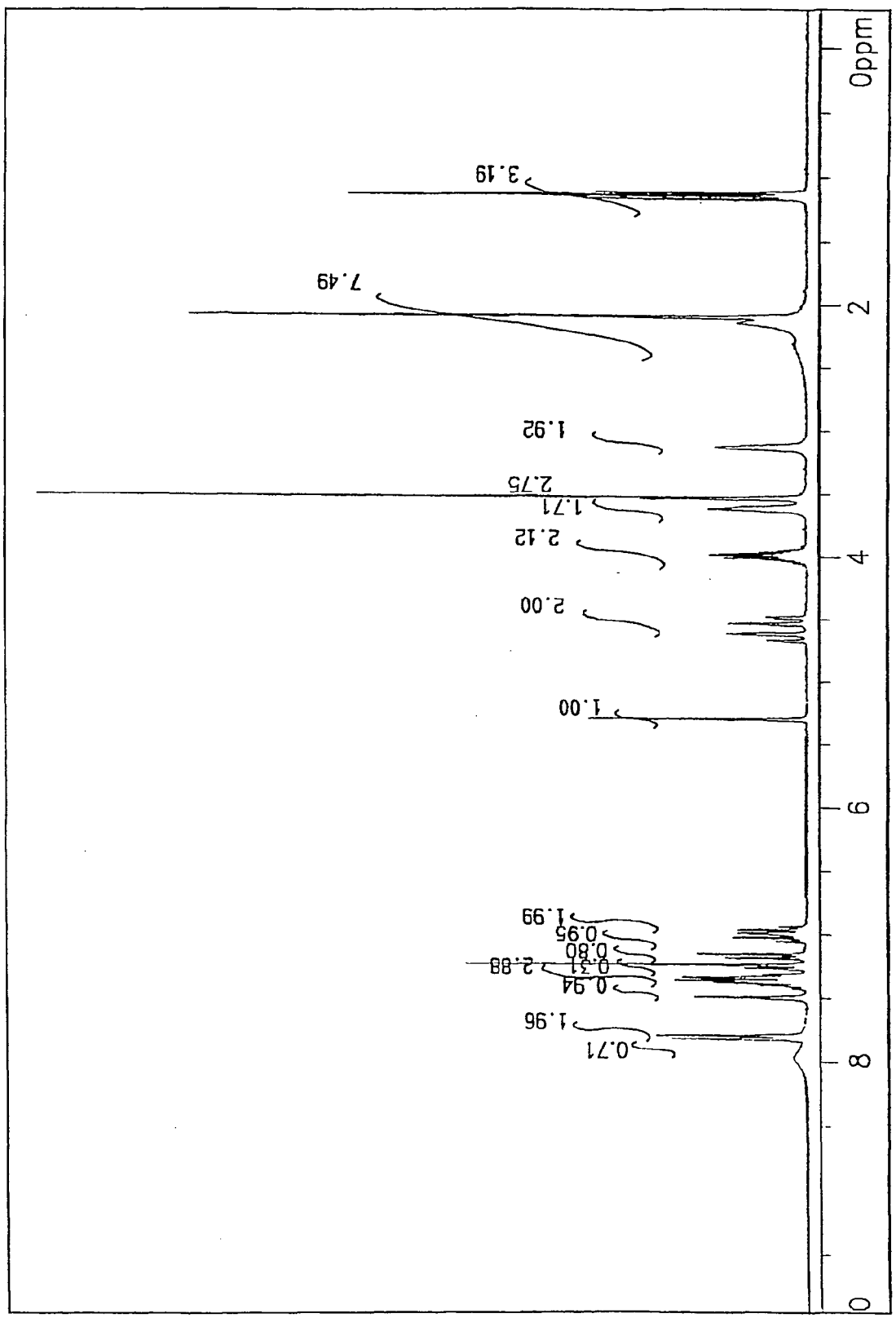
Figure 3D:
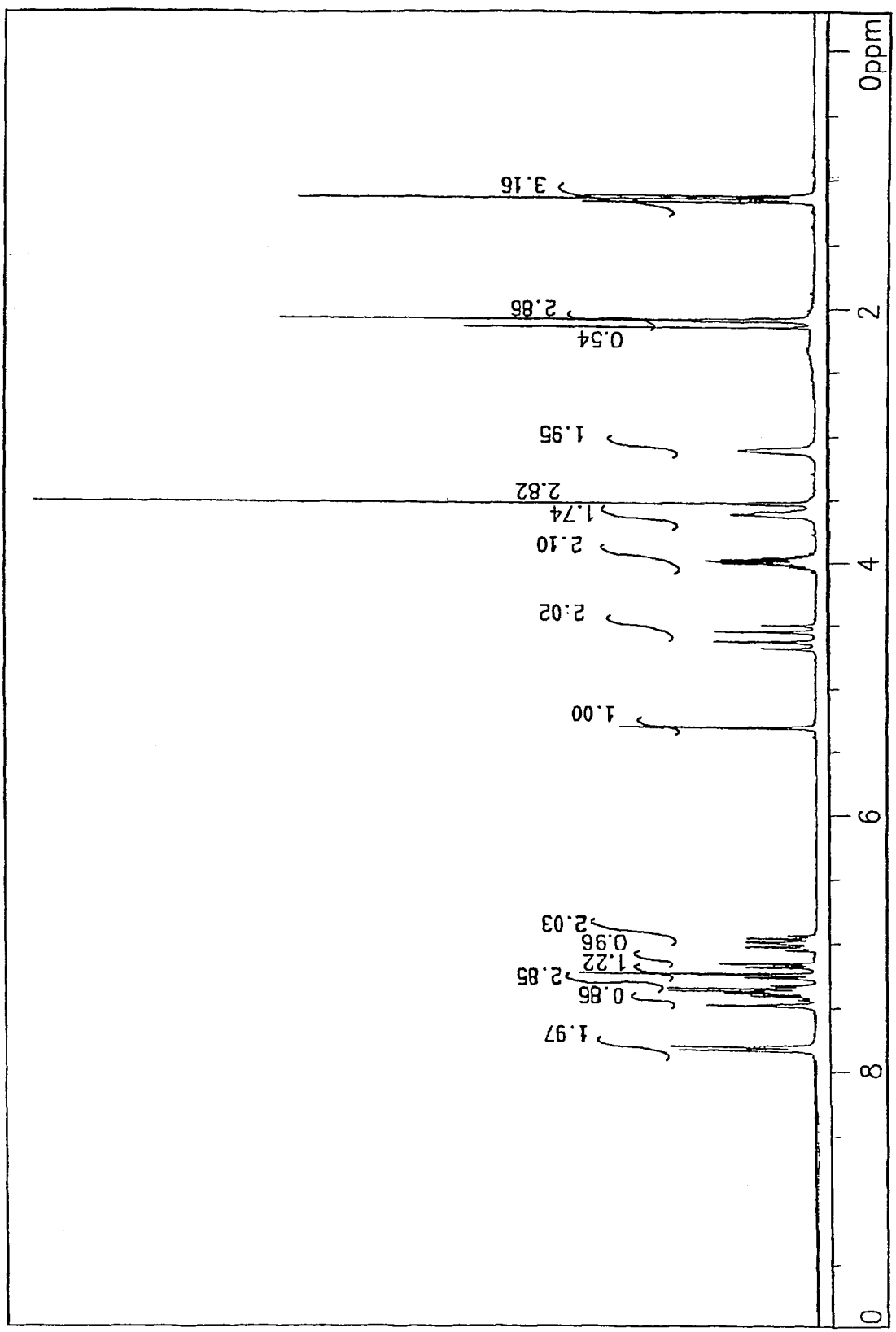

Photostability Test 1.0 g of S-(−)-amlodipine besylate prepared, using S-(−)-amlodipine, in accordance with U.S. Pat. No. 4,879,303 and 1.0 g of S-(−)-amlodipine nicotinate dihydrate obtained in Example 1, which were placed in glass schales (100×20 mm), were exposed at 25-30° C. for 3 weeks under an incandescent lamp (220V, 100 W) that was placed at 30 cm above the samples. As a result, S-(−)-amlodipine besylate was discolored to yellow, while there was no color change in S-(−)-amlodipine nicotinate dihydrate. FIG. 3A shows $^1$H-NMR charts of S-(−)-amlodipine besylate before the photostability test. FIGS. 3B and 3C show $^1$H-NMR charts of S-(−)-amlodipine besylate of 11 days and 3 weeks after the test, respectively. Further, when the resulting sample of 3 weeks after the test was dried under a reduced pressure at room temperature for 3 hours and the $^1$H-NMR was re-measured (FIG. 3D). The peaks on $^1$H-NMR of S-(−)-amlodipine besylate after the tests are as follows:

11 Days after the photostability test (FIG. 3B):
  broad peaks at 1.98 and 7.99 ppm
3 Weeks after the photostability test (FIG. 3C):
  no peak at 1.98 ppm and broad peaks at 2.15, 2.20 and 7.99 ppm,
Dried sample of 3 Weeks after the photostability test (FIG. 3D):
  no peak at 2.20 and 7.99 ppm and sharp peak at 2.15 ppm Therefore, a photostability problem of S-(−)-amlodipine besylate can be inferred from the above test result. Further, it is shown that S-(−)-amlodipine besylate absorbs about 1.5-2.5 of water contents during the photostability test.

Figure 4A:
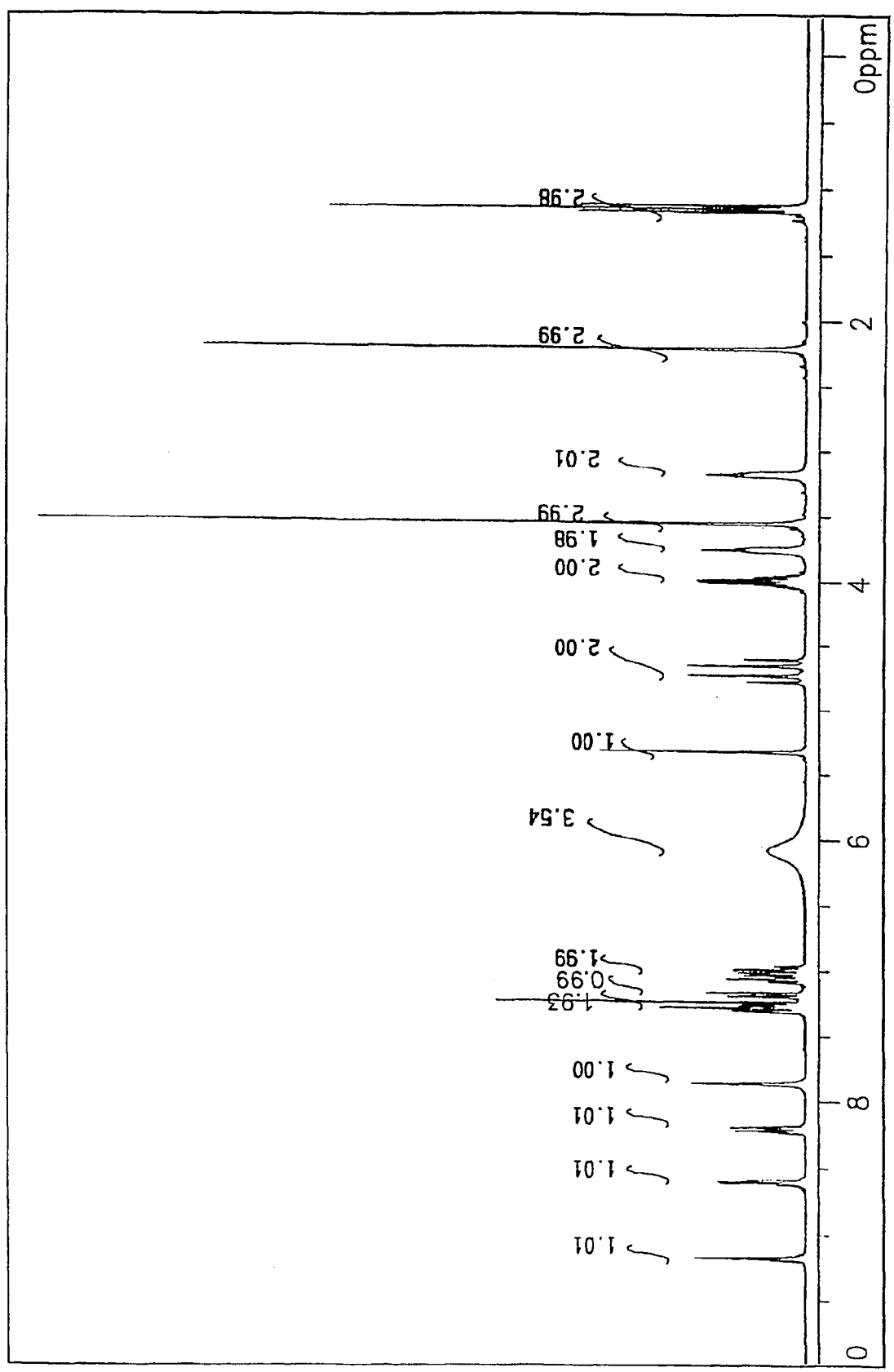
FIGS. 4A and 4B show $^1$H-NMR charts of S-(−)-amlodipine nicotinate before and after photostability test, respectively.
Figure 4B:
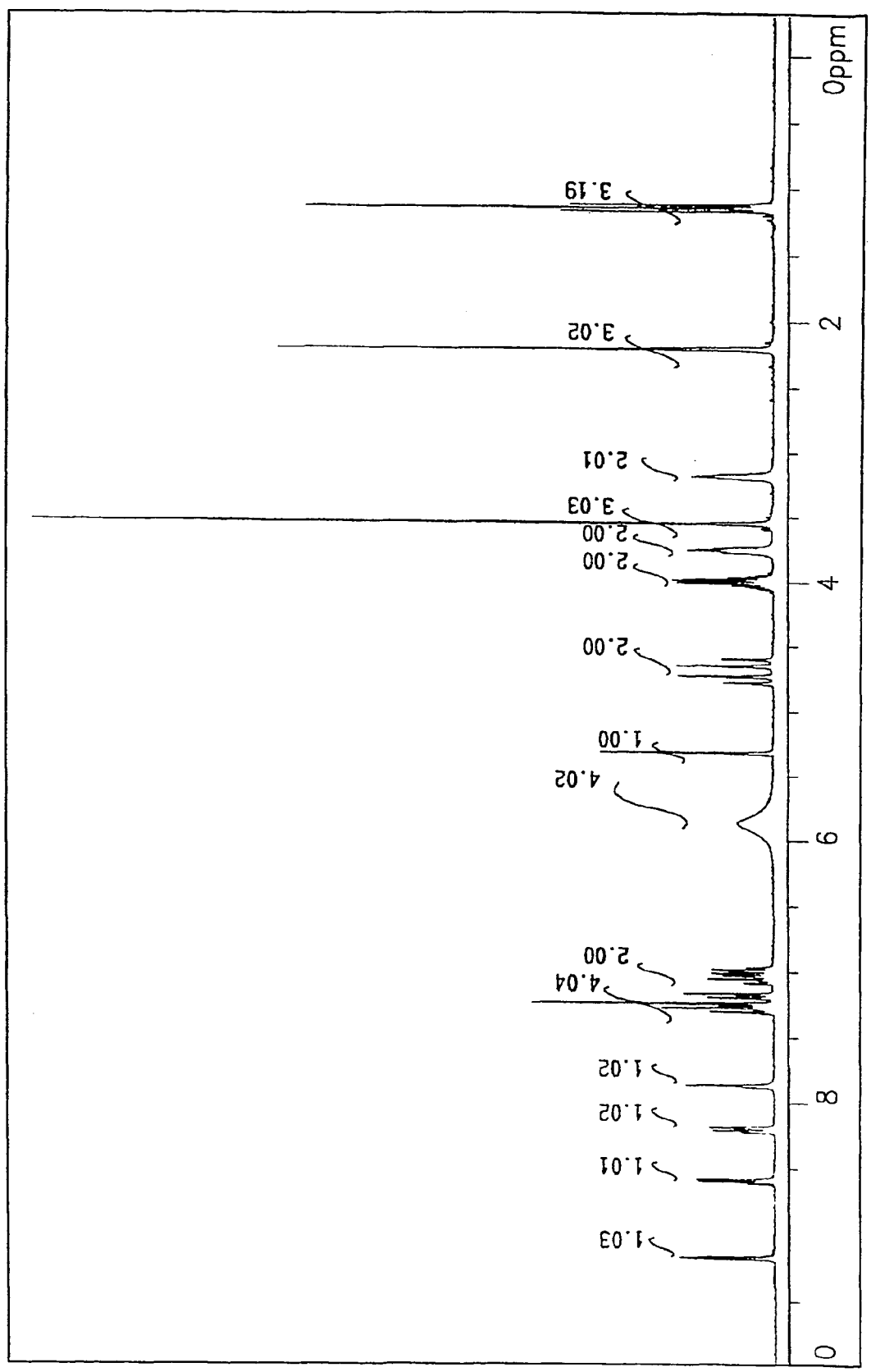

FIGS. 4A and 4B show H-NMR charts of S-(−)-amlodipine nicotinate before and after the photostability test, respectively. There is no significant difference in between FIG. 4A and FIG. 4B.

As clear from the results above, the nicotinic acid salt of S-(−)-amlodipine shows improved photostability.

TEST EXAMPLE 2

Comparison of Pharmacological effects Induced by Amlodipine Nicotinate and S-(−)-amlodipine Nicotinate Cardiovascular effects, i.e., in vivo anti-hypertensive activities, were measured for amlodipine nicotinate prepared in accordance with Example 1 except for using amlodipine and S-(−)-amlodipine nicotinate prepared in Example 1, using spontaneously hypertensive rats (SHRs), by Korea Research Institute of Chemical Technology (Screening Center, #100, Jang-dong, Yuseong-gu, Daejeon)

(1) Animal Used

Male SHRs (Charles Rever Co., Japan) aged 13-14 weeks were used. Before evaluation, the SHRs were accustomed in a clean breeding chamber under conditions of a temperature of 22.5±1° C., a relative humidity of 55±5% and a lighting time of 12 hour intervals.

The SHRs having a systolic blood pressure over 170 mmHg were divided into 7 groups, i.e., Test Groups 1 to 3 (for amlodipine nicotinate), Test Groups 4 to 6 (for S-(−)-amlodipine nicotinate) and a Control Group. Each Test Group and Control Group consisted of 6-8 SHRs (n=6-8).

(2) Preparation and Administration

The test compounds were dissolved in distilled water to prepare test solutions immediately prior to administration. The test solutions of amlodipine nicotinate and S-(−)-amlodipine nicotinate were prepared by dissolving 1, 3, and 10 mg/kg in distilled water (0.5 ml/100 g rat), respectively, and then administered orally to each Test Group. The vehicle (distilled water) was administered to Control Group.

(3) Measurement

The systolic blood pressure was measured with Multi-channel 8000 (TSE Co., Germany), using a tail-cuff method. That is, the systolic blood pressures of a tail artery of each rat were measured before the administration of the test solutions and after 2, 4, 6, 8, 10, and 24 hours from the administration thereof. In order to facilitate the measurement of blood pressures, the test animals of each Group underwent warming at 37° C. for about 10 minutes before the measurements.

(4) Statistical Processing Method

The results of the foregoing test were expressed by a mean percentage and standard error (mean %±S.E.M.). Statistical analysis of the test results were conducted by an unpaired t-test and ANOVA (one-way analysis of variance) with Sigma Stat program (Jandel Co., USA). The secondary evaluations were conducted by a Dunnett's multiple comparison test.

(5) Results

Figure 5:
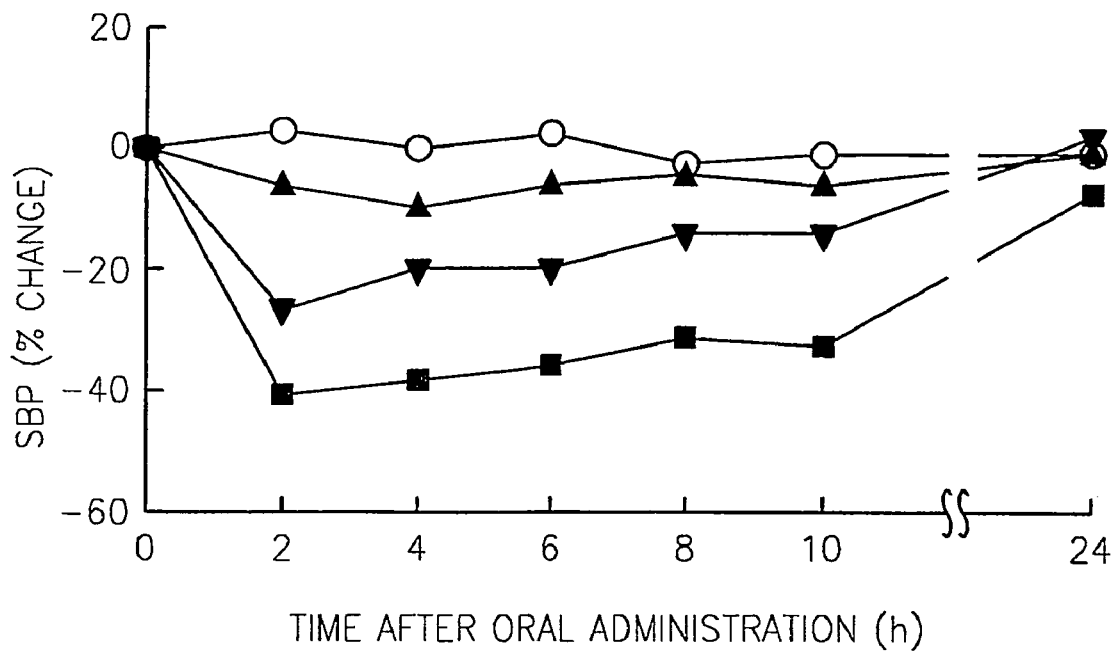
FIG. 5 is a graph illustrating the anti-hypertensive effects of amlodipine nicotinate on spontaneously hypertensive rats (Vehicle: O, Test Group 1 (1 mg/kg): ▼, Test Group 2 (3 mg/kg): ▲, and Test Group 3 (10 mg/kg): ■)
Figure 6:
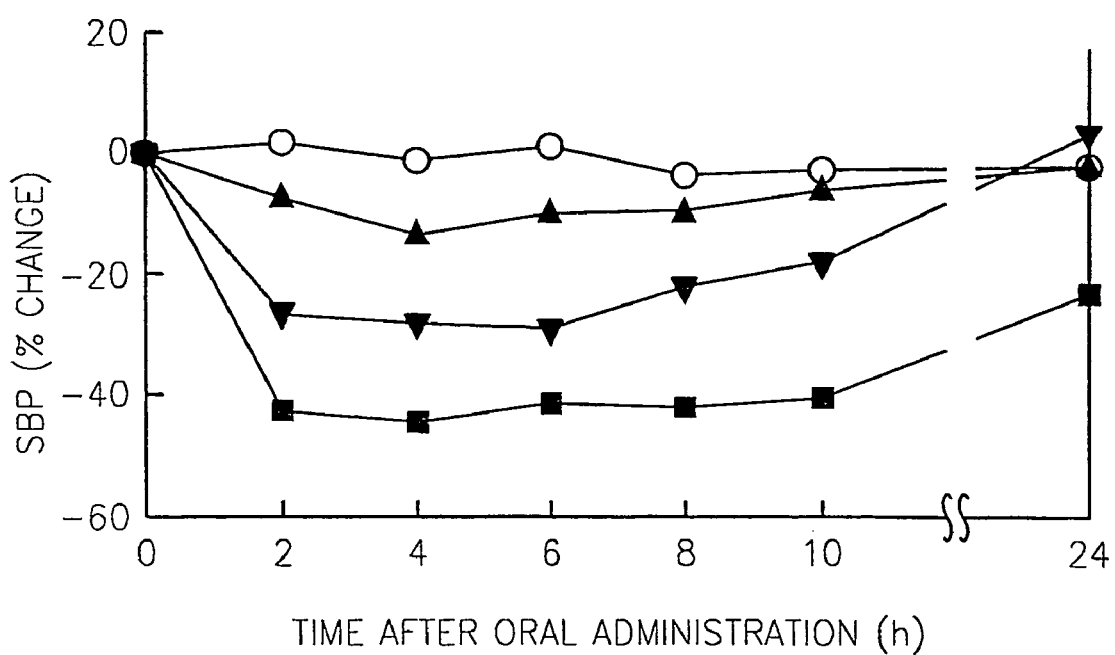
FIG. 6 is a graph illustrating the anti-hypertensive effects of S-(−)-amlodipine nicotinate on spontaneously hypertensive rats (Vehicle: O, Test Group 4 (1 mg/kg): ▲, Test Group 5 (3 mg/kg): ▼, and Test Group 6 (10 mg/kg): ■)
Figure 7:
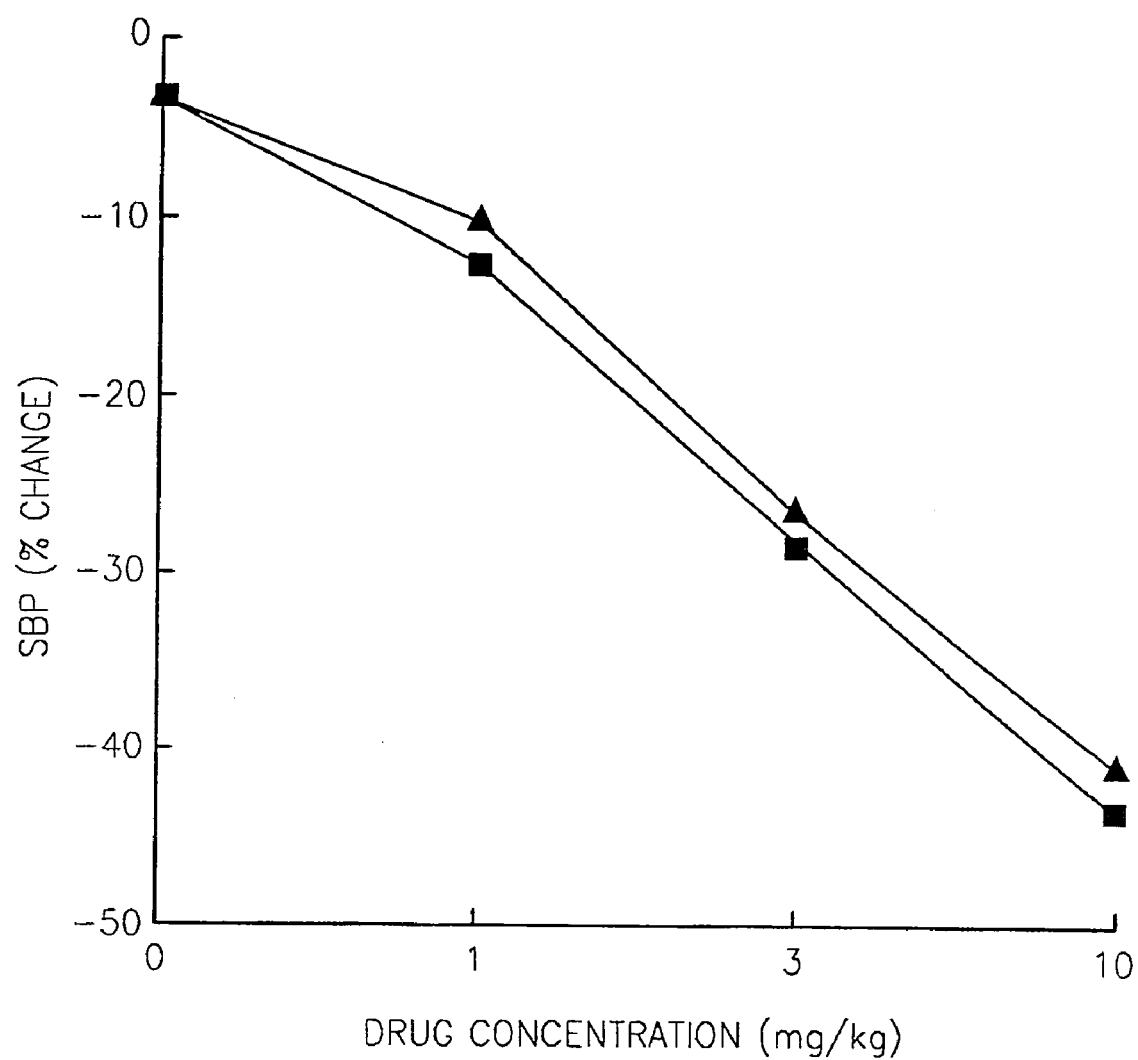
FIG. 7 shows dose-response curves for the maximal changes of systolic blood pressure of amlodipine nicotinate and S-(−)-amlodipine nicotinate in spontaneously hypertensive rats (Amlodipine nicotinate: ▲ and S-(−)-Amlodipine nicotinate: ■)

The test results are shown in FIGS. 5 to 7 and Tables 1 & 2. Both amlodipine nicotinate (FIG. 5 and Table 1) and S-(−)-amlodipine nicotinate (FIG. 6 and Table 1) dose-dependently reduced blood pressures. All Test Groups showed similar hypotensive (blood pressure falling) profiles. Substantial anti-hypertensive effects started to appear after 2 hours from the administrations and the maximal effects were displayed between 2 hours and 6 hours. The anti-hypertensive effects were maintained for over 10 hours. In Test Groups to which the doses of 10 mg/kg were administered (Test Groups 3 and 6), substantial anti-hypertensive effects were maintained even after 24 hours from administration.

The maximal anti-hypertensive effects of each Test Group are shown in Table 1 and FIG. 7.

TABLE 1

Maximal anti-hypertensive effects of each Test Group

| Dose | amlodipine nicotinate | S-(−)-amlodipine nicotinate | Intensity |
|---|---|---|---|
| 1 mg/kg (Group 1 & 4) | −10.20 ± 2.71 | −12.4 ± 1.73 | 1.22 |
| 3 mg/kg (Group 2 & 5) | −26.8 ± 3.22 | −28.3 ± 3.31 | 1.06 |
| 10 mg/kg (Group 3 & 6) | −40.9 ± 2.08 | −43.6 ± 1.65 | 1.07 |

In Table 1, the intensity is the percentage of the maximal effect of S-(−)-amlodipine nicotinate to the maximal effect of amlodipine nicotinate.

As shown in Table 1 and FIG. 7, substantial difference was shown in the Test Groups (Groups 1 & 4) to which the doses of 1 mg/kg were administered (p<0.05 vs. amlodipine nicotinate). The S-(−)-amlodipine nicotinate showed anti-hypertensive activity about 1.22 times higher than amlodipine nicotinate at 1 mg/kg dose.

The $ED_{20}$ values (the amount necessary for 20% decrease in the blood pressure) of amlodipine nicotinate and S-(−)-amlodipine nicotinate were 2.19±0.57 mg/kg and 1.91±0.49 mg/kg, respectively, as shown in Table 2.

TABLE 2

$ED_{20}$ values

| | Concentration (mg/kg) | Intensity |
|---|---|---|
| Amlodipine nicotinate | 2.19 ± 0.57 | 1.00 |
| S-(−)-Amlodipine nicotinate | 1.91 ± 0.49 | 1.15 |

In Table 2, the intensity is the reverse percentage of $ED_{20}$ value of S-(−)-amlodipine nicotinate to $ED_{20}$ value of amlodipine nicotinate.

As shown in Table 2, S-(−)-amlodipine nicotinate showed anti-hypertensive activity about 1.15 times higher than amlodipine nicotinate.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An S-(−)-amlodipine nicotinate in dihydrate form, having the X-ray diffraction pattern as shown in FIG. 1. wherein the S-(−)-amlodipine nicotinate is 3-ethyl 5-methyl-(−)2-[(2-aminoethoxy)methyl]-4-(2-chlorophenyl)-1,4-dihydro-6-methylpyridine-3,5-dicarboxylate nicotinate.

2. A pharmaceutical composition for anti-ischaemia or anti-hypertension comprising a therapeutically effective amount of S-(−)-amlodipine nicotinate and a pharmaceutically acceptable carrier, wherein the S-(−)-amlodipine nicotinate is 3-ethyl 5-methyl-(−)2-[(2-aminoethoxy)methyl]-4-(2-chlorophenyl)-1,4-dihydro-6-methylpyridine-3,5-dicarboxylate nicotinate.

* * * * *